United States Patent [19]

Pan et al.

[11] Patent Number: 5,183,941
[45] Date of Patent: Feb. 2, 1993

[54] HAIR DYE COUPLER COMPOUNDS

[75] Inventors: Yuh-Guo Pan, Stamford, Conn.; Alexander Chan, Mineola, N.Y.; Lana Hochman, Westport, Conn.

[73] Assignee: Clairol Incorporated, New York, N.Y.

[21] Appl. No.: 602,014

[22] Filed: Oct. 23, 1990

Related U.S. Application Data

[63] Continuation of Ser. No. 353,925, May 18, 1989, abandoned.

[51] Int. Cl.$^5$ .......................................... C07C 211/49
[52] U.S. Cl. ...................................................... 564/390
[58] Field of Search ................... 564/390, 223, 157; 544/165; 546/232, 233; 548/567, 569

[56] References Cited

U.S. PATENT DOCUMENTS

| | | | |
|---|---|---|---|
| 516,755 | 3/1894 | Brack et al. ........................ | 564/390 |
| 2,234,036 | 10/1939 | Zitscher et al. ..................... | 8/46 |
| 3,210,252 | 10/1965 | Blanke ................................ | 8/412 |
| 3,555,091 | 1/1971 | Benoit-Guyod et al. ............ | 564/223 |
| 3,622,629 | 11/1971 | Lugosy ............................... | 260/570 AB |
| 3,712,790 | 1/1973 | Kalopissis .......................... | 8/10.2 |
| 3,762,922 | 10/1973 | Lugosy et al. ..................... | 96/56 |
| 3,834,866 | 9/1974 | Pum ................................... | 8/11 |
| 4,065,255 | 12/1977 | Andrillon et al. .................. | 8/10.2 |
| 4,094,635 | 6/1978 | Bugaat et al. ...................... | 8/11 |
| 4,101,671 | 7/1978 | Keck et al. ......................... | 546/233 |
| 4,588,410 | 5/1986 | Konrad et al. ..................... | 8/421 |
| 4,797,130 | 1/1989 | Clausen et al. .................... | 8/421 |

OTHER PUBLICATIONS

J. F. Corbett, The Role of Meta Difunctional Benzene Derivatives in Oxidative Hair Dyeing. I. Reaction with p-Diamines, J. Soc. Cosmet. Chem., 24:103-134 (1973).
Chemistry of Synthetic Dyes, vol. 5, Ch. VII: J. F. Corbett, Hair Dyes (Academic Press 1971), pp. 475-534.

Primary Examiner—Joseph Paul Brust
Assistant Examiner—Jacqueline Haley
Attorney, Agent, or Firm—Charles J. Zeller

[57] ABSTRACT

The present invention concerns the aminophenols (I) as novel couplers

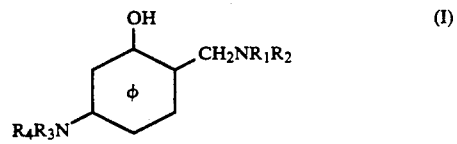

wherein $R_1$ and $R_2$ may be the same or different and are hydrogen, alkyl and hydroxyalkyl of from 1 to about 6 carbons in the alkyl moiety, or $R_1$ and $R_2$ can also form, together with the nitrogen atom to which they are attached, a morpholine, piperidine or pyrrolidine ring, and $R_3$ and $R_4$ are hydrogen, alkyl, acyl and hydroxyalkyl having from 1 to about 6 carbons, and oxidative hair dye compositions containing same along with at least one primary dye intermediate in aqueous or hydroalcoholic media.

9 Claims, No Drawings

HAIR DYE COUPLER COMPOUNDS

This application is a continuation of U.S. application Ser. No. 07/353,925 filed May 18, 1989, now abandoned.

FIELD OF INVENTION

This invention relates to aminophenol dye couplers useful in the coloring of keratin fibers, especially human hair. More specifically, the present invention concerns certain oxidation dye couplers in the aminophenol class that provide blue to violet dyeouts on hair dyed with p-phenylenediamines.

BACKGROUND OF INVENTION

Three classes of components are important in oxidative hair dyeing: primary intermediates, oxidants, and couplers. The primary intermediates are difunctional benzene derivatives capable of being oxidized with resultant development of color, e.g., ortho- and para-phenylenediamines and para-aminophenols.

Hydrogen peroxide is the usual oxidant, although persalts of various acids or solid organic peroxide adducts may be employed, especially where a solid oxidant is desired.

The third component type—the coupler—is important in hair coloring to produce color nuances necessary for the simulation of a natural hair color. Couplers do not undergo facile oxidation. Rather, it is believed that a coupler, which contains a strong electron donating group, provides a dye by reaction with electrophilic benzoquinoneimines. Thus, any aromatic compound having an amino or hydroxy group and an unblocked para position can react with a benzoquinoneimine to produce an indo dye. However, anilines and most monohydric phenols are usually insufficiently reactive to compete with the self-coupling reactions of the primary intermediates under hair dyeing conditions. For this reason, the most important couplers are phenols or anilines bearing a second strong electron donor in the meta position. See generally J. F. Corbett, *The Role of Meta Difunctional Benzene Derivatives in Oxidative Hair Dyeing. I. Reaction With p-Diamines*, J. Soc. Cosmet. Chem., 24, 103–134 (1973).

It is well known that the shade or color produced by a color coupler depends on its chemical nature. For example, with p-phenylenediamine as a primary intermediate, yellow to green/brown colors are produced by resorcinol couplers, red to red-violet colors are produced by m-aminophenol couplers and blue colors are produced by m-phenylenediamine and phenolic couplers.

In the important class of blue couplers, phenolic compounds in general form color far too slowly to be of practical commercial importance—the exception being 1-naphthol, which forms color at an acceptable rate, but has the disadvantage of poor solubility in hair dyeing systems, particularly in recently developed, highly aqueous systems. As an alternative, m-phenylenediamine couplers can be used. However, they have the disadvantage of producing dyes that slowly change color from blue to red over a period of days or weeks.

U.S. Pat. No. 4,797,130 to Clausen, et al. discloses compounds having the structures

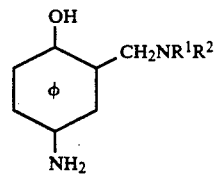

wherein the groups $R^1$ and $R^2$ may include hydrogen, alkyl, hydroxyalkyl, aminoalkyl, and the like. Unlike the dye coupler compounds of the present invention, the compounds (II) are primary intermediates, that is, color is developed by oxidizing these compounds, e.g., with hydrogen peroxide, to form benzoquinoneimines that are reactive with a color-producing coupler. Placement of the hydroxy and amino groups para to each other is essential for these compounds (II) to behave as primary intermediates.

U.S. Pat. No. 3,210,252 to Blanke, et al. discloses 5-amino-2-methylphenol as a coupler. When this coupler is used to couple with p-phenylenediamine, a red-violet shade is obtained on hair.

U.S. Pat. No. 4,065,255 to Andrillon, et al. discloses a coupler of the structure

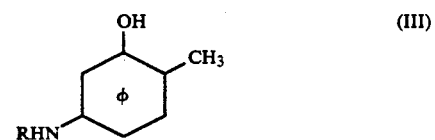

wherein R is a hydroxyalkyl of 1–4 carbon atoms. A red-violet color is obtained on gray hair when the coupler (III) with R defined as hydroxyalkyl containing 1 to 4 carbons is reacted with p-phenylenediamine U.S Pat. No. 4,588,410 to Konrad discloses couplers of the structure

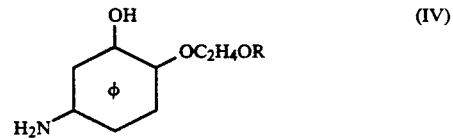

wherein R is hydrogen, methyl or hydroxyethyl. The compound (IV) is especially useful for providing red tones. More specifically, compound (IV) when R is hydrogen couples with p-phenylenediamine to give intense mahogany coloration on human hair.

U.S. Pat. No. 3,834,866 to Pum discloses 5-aminoguaiacol derivatives (V) useful as coupling agents

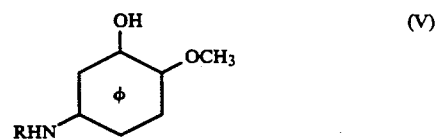

wherein when R is hydrogen, a dark maroon shade is produced with p-phenylenediamine on white virgin hair.

U.S. Pat. No. 3,712,790 to Kalopissis, et al. discloses the coupler

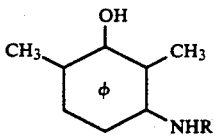

wherein R is hydrogen, alkyl, hydroxyalkyl, acyl, or N-alkylated or unsubstituted aminoalkyl or carbamylmethyl group, the alkyl groups of these radicals having 1-6 carbons.

U.S. Pat. No. 4,094,635 to Bugaut, et al. discloses m-aminophenol sulfonamide couplers in hair dye compositions. When reacted with p-phenylenediamine, a red-violet coloration on natural white hair is obtained.

It is apparent that m-aminophenols bearing a substituent ortho and para to the hydroxy and amino groups, respectively, produce red to red-violet colors with p-phenylenediamine. It is unexpected that when this substituent is an aminomethyl group, intense blue to blue-violet colors are obtained.

SUMMARY OF THE INVENTION

It is an object of this invention to provide hair dye couplers for use in oxidative hair dye compositions.

It is a primary object of the present invention to provide aminophenol dye couplers useful in oxidative hair dye compositions that produce blue to violet shades on hair when the primary intermediate is a p-phenylenediamine.

It is another object of the present invention to provide an oxidation hair coloring process suitable to provide hair with long-lasting natural color tones among which is a blue to violet color tone occasioned by the couplers of the present invention.

These and other benefits and advantages of the present invention are disclosed more fully in the detailed description of the invention, a summary of which follows.

In one aspect the present invention concerns novel compounds having the structure (I)

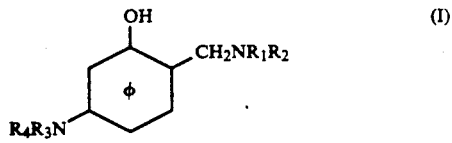

wherein $R_1$ and $R_2$ may be the same or different and are hydrogen, alkyl and hydroxyalkyl of from 1 to about 6 carbons, or $R_1$ and $R_2$ form, together with the nitrogen atom to which they are attached, a morpholine, piperidine or pyrollidine ring, and $R_3$ and $R_4$ are hydrogen, alkyl, acyl and hydroxyalkyl having from 1 to about 6 carbons.

A further aspect of the present invention concerns a dyeing composition useful in permanently dyeing keratin fibers including human hair, the dyeing composition comprising the coupler (I) and a primary intermediate.

In yet another aspect, the present invention concerns a process for permanently dyeing hair comprising admixing the dyeing composition with an oxidizer, applying the mixture for a predetermined period of time, and rinsing the mixture from the hair.

DETAILED DESCRIPTION OF INVENTION

The m-aminophenol compounds (I) of the present invention are quite suitable for use generally as dye couplers in oxidative dye compositions. The oxidative dye composition further contains a primary intermediate such as p-phenylenediamine, the composition being oxidizable with hydrogen peroxide or other oxidant to produce an array of colors. Especially suitable couplers (I) are
5-amino-2-[(dimethylamino)methyl]phenol;
5-amino-2-{[bis(2-hydroxyethyl)amino]methyl}phenol;
5-amino-2-(morpholinomethyl)phenol;
5-amino-2-(pyrrolidinomethyl)phenol;
5-amino-2-(aminomethyl)phenol;
5-dimethylamino-2-[(dimethylamino)methyl]phenol;
5-dimethylamino-2-(pyrrolidinomethyl)phenol;
5-acetamido-2-[(dimethylamino)methyl]phenol,
and their acid, especially hydrochloride, salts.

In a particularly useful and preferred aspect of the present invention, it has been found that certain of the m-aminophenol couplers (I) and their acid salts, when employed in an alkaline oxidizing medium with a suitable primary intermediate, especially p-phenylenediamine primary intermediates, unexpectedly impart to the keratin fibers a blue to violet shade. Moreover, it has also been found that surprisingly long-lasting keratin fiber shades are obtainable, which shades resist fading caused by weathering and/or light. In this regard, they are more long-lasting than the blue to violet shades obtained when m-phenylenediamines are employed as the coupler. The blue to violet shades produced by the couplers (I) when employed with p-phenylenediamines are particularly important to achieve a true black hair color having a realistic tonal impression.

It should be understood that the blue to violet colors referred to herein are the actual hues obtained when the hair is dyed with the coupler (I) as the only coupler and the suitable primary intermediate, i.e., a primary intermediate used in connection with this preferred aspect of the invention, such as p-phenylenediamine, that provides with a coupler (I) the blue to violet color to the hair fibers. The suitable primary intermediates may be easily determined by actual testing with the disclosed couplers of the present invention, in accordance with the procedures outlined in the examples. As one skilled in the art realizes, the color obtained by the mere admixture of the couplers (I) and the suitable primary intermediates under oxidative conditions is not necessarily the same hue obtained when used to actually dye hair. Of course, the couplers (I) and the suitable primary intermediates are seldom used independently of other dye constituents. Rather, as described elsewhere in this application, a plurality of couplers are used with one, two or more primary intermediates to obtain the desired color imparted to the hair, which color will be a blend of the aforementioned blue to violet shade as well as other shades provided by whatever additional constituents are present.

Particularly preferred couplers in this preferred aspect of the invention are
5-amino-2-[(dimethylamino)methyl]phenol;
5-amino-2-(pyrrolidinomethyl)phenol;
5-amino-2-(aminomethyl)phenol,
and their acid, especially hydrochloride, salts.

The dye compositions of the present invention comprise from about 0.001 to about 10%, preferably from about 0.05 to about 5%, most preferably from about 0.1 to about 2.5%, of a coupler, all or part of which coupler may be the coupler (I), from about 0.001 to about 10%, preferably from about 0.05 to about 5%, most preferably from about 0.2 to about 2.5%, of a primary intermediate, and water. The proportions and amounts of the several constituents in the hair dye composition will depend on the nature and amount of the dye components, the tonal impression to be created, and the color of the hair to be dyed. Whether to use two or more of the couplers or whether to include two or more primary intermediates will depend on the shade of the color desired. Generally, the coupler to primary intermediate molar ratio is from about 0.1:1 to about 10:1, preferably from about 1:1 to about 4:1.

The dye compositions of the present invention may comprise the coupler (I) and one or more additional coupler compounds, for example, m-phenylenediamines such as 2,4-diaminoanisole and 2,4-diaminophenoxyethanol; other m-aminophenols such as m-aminophenol, 5-amino-2-methylphenol, 5-(N-2-hydroxyethylamino)-2-methylphenol, 2-methyl-5-carbamylmethylaminophenol and 5-amino-2,6-dimethylphenol; m-acetamidophenols such as 5-acetamido-2-methylphenol; m-ureidophenols; resorcinols, and heterocyclic couplers such as 6-hydroxybenzomorpholine, 2,6-diaminopyrridine and 1-phenyl-3-methylpyrazolone.

The primary intermediates incorporated in the dye composition of the present invention are preferably p-phenylenediamines, for example, dye compounds of the formula

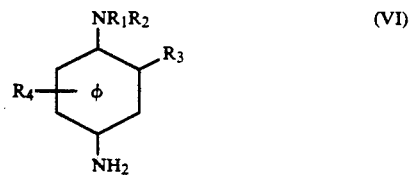

(VI)

wherein $R_1$ and $R_2$ are substituent groups including hydrogen, alkyl, hydroxyalkyl, aminoalkyl, and acylaminoalkyl, $R_3$ is hydrogen, alkyl, alkoxy or halogen, and $R_4$ is hydrogen, halogen, alkyl or alkoxy, the alkyls having from 1 to 6, preferably from 1 to 4 carbons, the compounds (VI) being as a free base or in the form of an acid additive salt such as a hydrochloride, and p-aminophenols, for example, dye compounds of the formula

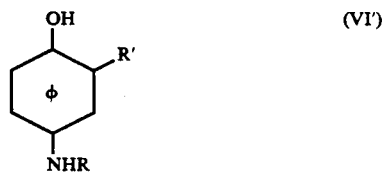

(VI')

wherein R and R' are hydrogen, alkyl, hydroxyalkyl, alkoxy, or halogen, the alkyls having 1 to 6 carbons.

Illustrative compounds (VI) are p-phenylenediamine, 2,6-dimethyl-3-methoxy-p-phenylenediamine dihydrochloride; 3-methoxy-4-amino-N,N-dimethylaniline sulfate; N,N-bis(2-hydroxyethyl)-p-phenylenediamine sulfate. Illustrative compounds (VI') are p-aminophenol; 4-amino-2,6-dimethylphenol; 4-[(2-acetamidoethyl)-amino]phenol sulfate; 3-methyl-4-aminophenol hydrochloride, and 2,5-dimethyl-4-aminophenol. p-Phenylenediamine, p-toluenediamine, p-aminophenol and N,N-bis(2-hydroxyethyl)-p-phenylenediamine sulfate are preferred.

Two or more primary intermediate compounds (VI) and (VI') may be incorporated into the dye compositions of the present invention. The hair dye composition disclosed herein may also include, in addition to the primary intermediate compounds (VI), one or more dyes such as anthraquinones, nitrobenzenes, diphenylamines, azo dyes, indoanilines, indophenols and indamines.

The dye compositions of the present invention include an aqueous, alcoholic or hydroalcoholic medium as a vehicle or carrier. The alcohol moiety, if present, is usually a lower alkanol, of from 1 to 6 carbons, especially ethanol or propanol, but may be a glycol having a total of up to about 10 carbons, especially less than 6 carbons, such as propylene glycol, butyl glycol and diethyleneglycol monobutyl ether. The vehicle is generally from about 1 to 75% by weight of the composition. Typically, the alcohol moiety, if present, comprises 10 to about 50% by weight of said vehicle, and the vehicle is typically from about 10 to about 50% by weight of the composition.

The compositions of the present invention may further include a cationic, anionic or amphoteric surface-active agent in an amount of up to about 20% by weight, preferably from about 0.5 to about 10%. Representative surface-active agents include octoxynol-1, nonoxynol-4, oleic acid and salts thereof and lauric acid and salts thereof.

The hair dye compositions of the present invention may also include one or more adjuvants such as perfumes, antioxidants such as sodium sulfite and sodium thioglycolate, sequestering agents such as EDTA, alkalizing agents such as ammonia or an alkanolamine, acidifying agents such as oleic, acetic acid and phosphoric acids. These adjuvants are present in an amount effective to provide their functional activity. The pH of the compositions of the present invention range typically from about 8 to about 11.

Although preferred to admix the developer, e.g., hydrogen peroxide, and the dyeing composition at the moment of use, compositions containing hydrogen peroxide are within the scope of this invention. The hydrogen peroxide developer is typically an aqueous solution of $H_2O_2$ having a concentration between 5 and 50 volumes, preferably between 10 and 40.

Upon mixing with the developer, the primary intermediate is oxidized and thereafter reacts with the coupler to provide the intended color. After mixing, the mixture is applied to hair for typically from about 5 to about 60 minutes, especially between about 20 and about 45 minutes. As known in the art, the dyeing composition often contains more than one primary intermediate and more than one coupler, to provide the shade of hair color desired.

The invention is further described by way of the examples below.

EXAMPLE 1

Synthesis of 5-amino-2-(aminomethyl)phenol Dihydrochloride (1) Synthesis of 5-acetamido-2-[(2-chloroacetamido)methyl]phenol A solution of 3-acetamidophenol (1.5 g, 10 mmol) and N-(hydroxymethyl)-2-chloroacetamide (1.2 g, 10 mmol) was stirred in 50 ml of 20% HCl in methanol at room temperature for 2 days. After removal of solvent, the desired product was isolated in 20% yield (0.51 g, 2 mmol) by chromatography (silica gel, eluted with ethyl acetate and hexane, 40/60).

(2) Hydrolysis of 5-acetamido-2-[(2-chloroacetamido)methyl]phenol

5-Acetamido-2-[(2-chloroacetamido)methyl]phenol (0.51 g, 2 mmol) was hydrolyzed in 10 ml of 20% HCl in methanol at 80° for 1 hour. 5-Amino-2-(aminomethyl)phenol was isolated in 90% yield (0.36 g, 1.8 mmol) as its dihydrochloride salt. Its NMR ($D_2O$) was $\delta$7.2(d, J=7.5 Hz, 1H), 6.7(d, J=7.5 Hz, 1H), 6.6(6s, H), 3.9(6s, 2H).

EXAMPLE 2

Synthesis of 5-dimethylamino-2-[(dialkylamino)methyl]phenol

An equimolar solution of 3-dimethylaminophenol, formaldehyde and a secondary amine recited below in Table I was stirred in methanol at room temperature until there was no further reaction. The Mannich base was isolated by filtration and purified by recrystallization.

TABLE I

| Secondary Amine | Product | Yield % |
|---|---|---|
| Morpholine | 5-dimethylamino-2-(morpholinomethyl)phenol* | 80 |
| Dimethylamine | 5-dimethylamino-2-[(dimethylamino)methyl]phenol** | 70 |

*NMR (acetone - $d_6$) $\delta$6.8(d, J = 6 Hz, 1H), 6.1(m, 2H), 3.6 (m, 4H), 3.5(s, 2H), 2.8(s, 6H), 2.5(m, 4H)
**NMR (acetone - $d_6$) $\delta$6.8(d, J = 10 Hz, 1H), 6.2(m, 2H), 3.7(s, 2H), 2.9(s, 6H), 2.3(s, 6H)

EXAMPLE 3

Synthesis of 5-amino-2-[(dialkylamino)methyl]phenol dihydrochloride (1) Synthesis of 5-acetamido-2-[(dialkylamino)methyl]phenol An equimolar solution of 3-acetamidophenol, formaldehyde and a secondary amine recited in Table II below was stirred in methanol at room temperature until there was no further reaction. The Mannich base was isolated by filtration and purified by recrystallization.

(2) Hydrolysis of 5-acetamido-2-[(dialkylamino)methyl]phenol

5-Acetamido-2-[(dialkylamino)methyl]phenol was hydrolyzed in 20% HCl in methanol at 80° for 1 hour. 5-Amino-2-[(dialkylamino)methyl]phenol was isolated as its dihydrochloride salt.

TABLE II

| Amine | Product | Yield |
|---|---|---|
| Pyrrolidine | 5-acetamido-2-(pyrrolidinomethyl)phenol* | 44 |
| Diethanolamine | 5-acetamido-2-{[bis(2-hydroxyethyl)amino]methyl}phenol** | 73 |

*NMR (acetone - $d_6$) $\delta$9.8(6s, 1H), 7.2(6s, 1H), 7.0–6.8(m, 2H), 3.7(6s, 2H), 2.6(6s, 4H), 2.1(6s, 3H), 1.8(6s, 4H)
**NMR (acetone - $d_6$) $\delta$10.3(6s, 1H), 9.0(6s, 1H), 7.5(d, J = 3 Hz, 1H), 7.3(d, J = 8 Hz, 1H), 7.0(dd, J = 8 Hz, J = 3Hz, 1H), 4.3(d, J = 3 Hz, 2H), 3.8(m, 4H), 3.2(m, 4H), 2.0(s, 3H)

EXAMPLE 4

Synthesis of 5-amino-2-[(dimethylamino)methyl)]phenol Dihydrochloride

Acetic anhydride (21.2 ml, 220 mmol) was slowly added to a suspension of m-aminophenol (24.0 g, 220 mmol) in 60% of crushed ice and 60 ml of cold water. The reaction mixture was vigorously stirred for 30 minutes. The white precipitate was filtered, washed with cold water, and air-dried to give 30.5 g (92%) of pure 3-acetamidophenol, m.p. 147–149° C.

To a solution of 3-acetamidophenol (15.25 g, 101 mmol) in 40% dimethylamine (13.8 ml, 122 mmol) and 13 ml of methanol, was added 37% formalin (8.3 ml, 101 mmol). The reaction mixture was placed in an ice bath just after the precipitate formed (about 15—30 minutes). The white precipitate was filtered after 10–30 minutes, washed with cold water, and air-dried to give 13.7 g (65%) of 5-acetamido-2-[(dimethylamino)methyl]phenol, m.p. 133–135° C.

5-acetamido-2-[(dimethylamino)methyl)]phenol (5.0 g, 24 mmol) was dissolved in 30 ml of HCl/methanol (about 22%) and refluxed at 80° C. (oil bath) for 1.5 hours. The white compound, which precipitated out of solution, was filtered to give 4.4 g (77%) of 5-amino-2-[(dimethylamino)methyl]phenol dihydrochloride (m.p. 185–190° C.). Its NMR ($D_2O$) was $\delta$6.7(d, J=8 Hz), 6.2(d, J=2 Hz), 6.0(dd, J=8 Hz, J=2 Hz, 1H), 2.0(s, 3H).

The examples that follow demonstrate the use of the m-aminophenol dye couplers of the present invention. Examples 11–15 illustrate the preferred embodiment of the present invention, wherein certain compounds (I) provide, with p-phenylenediamine, a distinctively blue color when applied to hair.

EXAMPLE 5

5-Dimethylamino-2-[(dimethylamino)methyl]phenol (0.7%) was mixed with p-phenylenediamine (0.3%) in aqueous ethanol (water:ethanol=2:1 v/v). After mixing with equal volume of hydrogen peroxide (30 volume), and adjusting the pH to 10 with ammonium hydroxide, the mixture was applied to gray hair for 30 minutes. A red-violet shade was obtained after shampoo and rinse.

EXAMPLE 6

A water/ethanol (2:1 v/v) solution containing 0.7% p-phenylenediamine and 1% 5-amino-2-(morpholinomethyl)phenol was mixed with equal volume of hydrogen peroxide (30 volume). Ammonium hydroxide was used to raise the pH to 10. The final solution was employed to treat blended gray hair for 30 minutes. This imparted a red-violet color on the tress after shampoo and rinse.

EXAMPLE 7

An aqueous solution of p-phenylenediamine (0.16%) and 5-amino-2-{[bis(2-hydroxyethyl)amino]methyl}phenol dihydrochloride (0.6%) was prepared. An equal part of 20-volume hydrogen peroxide was added, and the pH was adjusted to 9.7 with monoethanolamine (MEA). This mixture applied for 30 minutes to gray hair imparted, after rinsing and shampooing, a purple color.

EXAMPLE 8

The same as Example 7 but with 5-acetamido-2-[(dimethylamino)methyl]phenol as the coupler. A light brown color was obtained on gray hair after 30 minutes of treatment.

EXAMPLE 9

The same as Example 7 but with 5-dimethylamino-2-(morpholinomethyl)phenol as the coupler. A light brown color was imparted on gray hair.

EXAMPLE 10 p-Aminophenol (0.22%) and 5-amino-2-[(dimethylamino)methyl]phenol dihydrochloride (0.48%) were dissolved in an aqueous medium. After mixing with an equal part of 20-volume hydrogen peroxide, the pH was raised to 10 with MEA. This final solution was used to dye gray hair. After 30 minutes the hair was rinsed and shampooed. The hair had a natural brown tone.

EXAMPLE 11 p-Phenylenediamine (0.16% by wt.) and 5-amino-2-[(dimethylamino)methyl]phenol dihydrochloride (0.48% by wt.) were dissolved in an aqueous solution. An equal part of 20-volume hydrogen peroxide was added, and the pH of this mixture was adjusted to about 9 with concentrated ammonium hydroxide. This final solution was applied to treat gray hair for 30 minutes to give a blue-violet color after shampooing. When the abovementioned phenol was replaced with 5-amino-2-methylphenol, a red-violet shade was obtained, as indicated in Table III below.

TABLE III

| Coupler | Hunter Tristmulus Values | | |
|---|---|---|---|
| | L | a | b |
| 5-amino-2-[(dimethylamino)methyl]phenol.2HCl | 13.8 | 6.0 | −8.0 |
| 5-amino-2-methylphenol | 11.7 | 9.4 | −0.1 |

In the Hunter system, the L value indicates intensity of the color obtained. The lower the value, the darker the color. The a value indicates the degree of redness or greenness of the color obtained. The higher the a value, the redder the color. The lower the a value, the greener the color. Similarly, the b value indicates the degree of yellowness or blueness of the color. The higher the b value, the more yellow the color obtained, while a low b value signifies a more blue color. As seen from Table III, the color obtained for 5-amino-2-[(dimethylamino)methyl]phenol dihydrochloride is significantly less red and more blue than that obtained with the conventional 5-amino-2-methylphenol coupler.

EXAMPLE 12

The following composition was mixed with an equal volume of 20-volume hydrogen peroxide and left on bleached hair for 30 minutes:

| | Wt. (gm.) |
|---|---|
| p-phenylenediamine | 0.27 |
| 5-amino-2-[(dimethylamino)methyl]phenol.2HCl | 0.6 |
| Sodium lauryl sulfate | 3 |
| Oleic acid | 20 |
| Propylene glycol | 8 |
| Octoxynol-1 | 9 |
| Isopropyl alcohol | 8 |
| Ammonium hydroxide | 8 |
| Erythorbic acid | 0.3 |

| | Wt. (gm.) |
|---|---|
| Water | Q.S. 100 |

After rinsing and shampooing, a blue-violet color was obtained on the hair.

EXAMPLE 13 p-Phenylenediamine (0.27%) and 5-amino-2-(pyrrolidinomethyl)phenol dihydrochloride (0.9%) were dissolved in an ethanolic solution (water:ethanol=7:3 v/v). An equal part of 20-volume hydrogen peroxide was added, and the pH of this mixture was brought up to about 9.6 with concentrated ammonium hydroxide. This solution was applied to regular gray hair for 30 minutes and a blue-violet shade was obtained.

EXAMPLE 14 p-Phenylenediamine dihydrochloride (0.3%) and 5-amino-2-(aminomethyl)phenol (0.35%) were mixed in an ethanolic solution (water:ethanol=75:25 v/v). Three parts of this solution and two parts of a 20-volume hydrogen peroxide were then combined, and the pH was adjusted to 9.7 with concentrated ammonium hydroxide. A violet color developed on gray hair after 30 minutes, while p-phenylenediamine with 5-amino-2-methylphenol gave a color having a more reddish hue. Tristimulus measurements of these two tresses again show that the tress dyed with the coupler of the present invention has a lower a value, i.e., less red hue (more blue hue), than the tress dyed with the conventional m-aminophenol coupler.

EXAMPLE 15

N,N-bis(2-hydroxyethyl)-p-phenylenediamine sulfate (0.45%) was used to replace p-phenylenediamine in Example 11. The mixture applied for 30 minutes to gray hair imparted, after rinsing and shampooing, a blue coloration.

We claim:

1. An oxidative hair dye coupler compound including its acid salts having the structure:

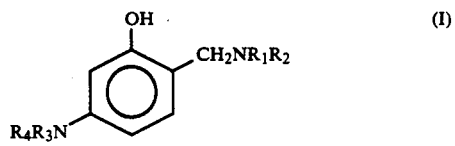

wherein $R_1$ and $R_2$ may be the same or different and are hydrogen or alkyl of from 1 to 6 carbons in the alkyl moiety, and $R_3$ and $R_4$ are hydrogen, alkyl and hydroxyalkyl, the alkyl group having from 1 to 6 carbons, said compound (I), when coupled with a paraphenylenediamine primary intermediate providing a dye characterized by a blue to blue-violet color.

2. The compound of claim 1 wherein $R_1$ and $R_2$ are selected from the group consisting of hydrogen and methyl and wherein $R_3$ and $R_4$ are selected from the group consisting of hydrogen and methyl.

3. The compound of claim 2 wherein $R_3$ is hydrogen.

4. The compound of claim 3 wherein $R_4$ is hydrogen.

5. The compound of claim 3 or 4 wherein $R_1$ is hydrogen.

6. The compound of claim 3 or 4 wherein $R_1$ is methyl.

7. The compound of claim 3 wherein $R_1$ and $R_2$ are methyl.

8. The compound of claim 1 which is 5-amino-2[(dimethylamino)methyl]phenol or its acid salts.

9. The compound of claim 1 which is 5-amino-2-(aminomethyl)phenol or its acid salts.

* * * * *